United States Patent

Crum et al.

[11] Patent Number: 5,907,050
[45] Date of Patent: May 25, 1999

[54] PROCESS FOR CONVERTING POLYMERIC SILICON CONTAINING COMPOUNDS TO MONOSILANES

[75] Inventors: Bruce Robert Crum, Madison, Ind.; Steven Kerry Freeburne, Edgewood; Larry Herbert Wood, Campbellsburg, both of Ky.

[73] Assignee: Dow Corning Corporation, Midland, Mich.

[21] Appl. No.: 09/163,492

[22] Filed: Sep. 30, 1998

[51] Int. Cl.$^6$ .................................................. C07F 7/08
[52] U.S. Cl. ........................................... 556/468; 556/467
[58] Field of Search ..................................... 556/468, 467

[56] References Cited

U.S. PATENT DOCUMENTS

| | | | |
|---|---|---|---|
| 2,380,995 | 8/1945 | Rochow | 260/607 |
| 2,488,487 | 11/1949 | Barry et al. | 260/448.2 |
| 2,598,435 | 5/1952 | Mohler et al. | 260/448.2 |
| 2,606,811 | 8/1952 | Wagner | 23/14 |
| 2,681,355 | 6/1954 | Barry et al. | 260/448.2 |
| 3,639,105 | 2/1972 | Atwell et al. | 23/366 |
| 4,079,071 | 3/1978 | Neale | 260/448.2 |
| 4,393,229 | 7/1983 | Ritzer et al. | 556/430 |
| 5,175,329 | 12/1992 | Bokerman et al. | 556/467 |
| 5,326,896 | 7/1994 | Chadwick et al. | 556/468 X |
| 5,430,168 | 7/1995 | Ferguson et al. | 555/467 |
| 5,606,090 | 2/1997 | Brinson et al. | 556/467 |

*Primary Examiner*—Paul F. Shaver
*Attorney, Agent, or Firm*—Melvin D. Fletcher

[57] ABSTRACT

A process for converting a high-boiling fraction resulting from the reaction of methyl chloride with silicon metalloid in a process typically referred to as the "direct process" to monosilanes. The process comprises forming a mixture comprising a low-boiling fraction comprising monosilanes and a high-boiling fraction comprising polymeric silicon containing compounds and contacting the mixture with hydrogen gas in the presence of a catalyst effective in promoting conversion of the polymeric silicon containing compounds to monosilanes. The process results in conversion of the high-boiling fraction to monosilanes. At least a portion of the catalyst present may be formed in situ during conduct of the direct process and isolation of the fractions.

19 Claims, No Drawings

PROCESS FOR CONVERTING POLYMERIC SILICON CONTAINING COMPOUNDS TO MONOSILANES

BACKGROUND OF INVENTION

The present invention is a process for converting a high-boiling fraction, resulting from the reaction of methyl chloride with silicon metalloid in a process typically referred to as the "direct process", to monosilanes. The process comprises forming a mixture comprising a low-boiling fraction comprising monosilanes and a high-boiling fraction comprising polymeric silicon containing compounds and contacting the mixture with hydrogen gas in the presence of a catalyst effective in promoting conversion of the polymeric silicon containing compounds to monosilanes. The present process results in conversion of the high-boiling fraction to monosilanes. At least a portion of the catalyst required for conduct of the process may be formed in situ during conduct of the direct process and isolation of the fractions.

In the preparation of methyl chlorosilanes by the direct process a complex mixture is formed which is typically distilled to separate methylchlorosilanes from other components present in the mixture. After the methylchlorosilanes are distilled from the mixture, remaining are monosilane and disilane by-product fractions. The monosilane fraction which boils below about 45° C. is hereinafter referred to as "low-boiling fraction" and the disilane fraction which boils above about 80° C. is hereinafter referred to as "high-boiling fraction." In current commercial operations for performing the direct process, the high-boiling fraction alone can constitute as much as five weight percent of the resultant product. Therefore, it is desirable to convert the high-boiling fraction along with the low-boiling fraction into commercially desirable products to reduce by-product disposal and to improve raw material utilization.

The "direct process" is well described in the patent literature, for example, in Rochow, U.S. Pat. No. 2,380,995 and Barry et al., U.S. Pat. No. 2,488,487. The high-boiling fraction remaining after the monosilanes overhead distillation is a complex mixture comprising higher boiling silicon containing compounds which have, for example, SiSi, SiOSi, and SiCSi linkages in the molecules. The high-boiling fraction may also contain particulate silicon and metals or compounds thereof. Typical high-boiling residues obtained from the direct process distillation product are described, for example, in Mohler et al., U.S. Pat. No. 2,598,435 and Barry et al., U.S. Pat. No. 2,681,355.

Wagner, U.S. Pat. No. 2,606,811, teaches a hydrogenation process where a compound containing a halogen and the Si—Si bond is heated to a temperature of at least 300° C. in the presence of hydrogen. The resultant products are monosilanes.

Atwell et al., U.S. Pat. No. 3,639,105, describe a process where hydrosilanes are produced by contacting a disilane with hydrogen gas under pressure and heating the mixture in the presence of a transition metal catalyst such as palladium on charcoal. Atwell et al. state that the disilane may be part of a mixture from the direct process. Atwell et al. further report that when the disilane was a methylchlorodisilane, the resulting product contained about four to 28 weight percent methyltrichlorosilane. Generally, organotrihalosilanes such as methyltrichlorosilane have limited commercial usefulness and for this reason limit the usefulness of the process described by Atwell et al.

Neale, U.S. Pat. No. 4,079,071, describes a process for preparing hydrosilanes in high yields by reacting methylchloropolysilanes with hydrogen gas under pressure at a temperature of from 25° C. to about 350° C. in the presence of a copper catalyst. Neale states that the methylchloropolysilanes can be those typically created as direct process by-products. Useful copper catalysts described by Neale include copper metal, copper salts, and complexes of copper salts with organic ligands. In some cases, Neale reports that up to 29 weight percent methyltrichlorosilane was formed.

Ritzer et al., U.S. Pat. No. 4,393,229, describe a process for converting alkyl-rich disilanes in a residue obtained from the manufacture of alkylhalosilanes to halogen-rich polysilanes. The process comprises treating an alkyl-rich disilane-containing residue with an alkyltrihalosilane or silicon tetrahalide in the presence of a catalyst and a catalytic amount of a hydrosilane reaction promoter at an elevated temperature. Ritzer et al. teach aluminum trichloride as a useful catalyst in their process when used with a hydrosilane promoter. Ritzer et al. further teach that the resulting halogen-rich polysilanes can, in a separate step, be cleaved to form monosilanes.

Bokerman et al., U.S. Pat. No. 5,175,329, describe a process for the production of organosilanes from the high-boiling residue resulting from the direct process that results in a net consumption of organotrichlorosilane. In the process, the high-boiling residue is contacted with an organotrichlorosilane and hydrogen gas in the presence of both a hydrogenation catalyst and a redistribution catalyst.

Ferguson et al., U.S. Pat. No. 5,430,168, describe a process for the production of monosilanes from the high-boiling residue resulting from the "direct process." The process comprises forming a mixture comprising an organotrihalosilane and high-boiling residue in the presence of hydrogen gas and a catalytic amount of aluminum trichloride. The process results in consumption of the organotrihalosilane and conversion of the high-boiling residue to useful monosilanes.

The present invention provides a process where a high-boiling fraction comprising polymeric silicon containing compounds resulting from producing methyl chlorosilanes is converted into commercially useful monosilanes. The present inventors have discovered that by forming a mixture comprising a low-boiling distillation fraction comprising monosilanes resulting from the reaction of methyl chloride with silicon metalloid and a high-boiling distillation fraction comprising polymeric silicon containing compounds, that the high-boiling fraction is converted to useful monosilanes. Furthermore, at least a portion of the catalyst in the present process can be formed in situ during conduct of the direct process and isolation of the resulting monosilanes.

SUMMARY OF INVENTION

The present invention is a process for converting a high-boiling fraction, resulting from the reaction of methyl chloride with silicon metalloid in a process typically referred to as the direct process, to monosilanes. The process comprises forming a mixture comprising a low-boiling fraction comprising monosilanes and a high-boiling fraction comprising polymeric silicon containing compounds and contacting the mixture with hydrogen gas in the presence of a catalyst effective in promoting conversion of the polymeric silicon containing compounds to monosilanes. The present process results in conversion of the high-boiling fraction to monosilanes. At least a portion of the catalyst present in the process may be formed in situ during conduct of the direct process and isolation of the fractions.

DESCRIPTION OF INVENTION

The present invention is a process for converting a low-boiling fraction and a high-boiling fraction resulting from the reaction of methyl chloride with silicon metalloid to form monosilanes. The process comprises forming a mixture comprising a low-boiling fraction comprising monosilanes having a boiling point below about 45° C. resulting from the reaction of methyl chloride with silicon metalloid and a high-boiling fraction comprising polymeric silicon containing compounds having a boiling point above 80° C. resulting from the reaction of methyl chloride with silicon metalloid. The mixture is contacted with hydrogen gas at a pressure of about 345 kPa to 68,948 kPa in the presence of a catalyst effective in promoting conversion of the polymeric silicon containing compounds to monosilanes at a temperature within a range of about 150° C. to 500° C.

The present process may be run in any standard pressurizable reactor suitable for contact with chlorosilanes. The process may be run as a batch process or as a continuous process. The process may be run, for example, in a continuous stirred-tank reactor, a bubble-column reactor, a trickle-bed reactor, or a plug-flow reactor.

The present process is useful for converting a high-boiling fraction resulting from the reaction of methyl chloride with silicon metalloid to useful monosilanes. The direct process for reacting methyl chloride with silicon metalloid, produces a mixture of methylchlorosilanes, methylchlorodisilanes, and silmethylenes. This mixture is then distilled to produce relatively pure dimethyldichlorosilane, methyltrichlorosilane, trimethylchlorosilane and methyldichlorosilane. The remaining by-product stream can be further distilled to produce a low-boiling fraction and a high-boiling fraction. The low-boiling fraction comprises monosilanes having a boiling point below about 45° C. For example, a typically weight percent composition of a low-boiling fraction resulting from the reaction of methyl chloride with silicon metalloid is 4 wt % methylchloride, 1 wt % methylchlorosilane, 18 wt % tetramethylsilane, 13 wt % trichlorosilane, 41 wt % dimethylchlorosilane, 0.4 wt % methyldichlorosilane, and 23 wt % isopentane.

The high-boiling fraction comprises polymeric silicon containing compounds having a boiling point above 80° C. The present process is useful for converting this high-boiling fraction to useful monosilanes. The polymeric silicon containing compounds include disilanes, such as, $Me_2ClSiSiClMe_2$, $Me_2ClSiSiMeCl_2$, $MeCl_2SiSiMeCl_2$, and silmethylenes, such as $Me_2ClSiCH_2SiClMe_2$, $Me_2ClSiCH_2SiCl_2Me$, and $MeCl_2SiCH_2SiCl_2Me$. A typical composition for such a high-boiling fraction comprises: 50–60 wt % of disilanes of formula $Si_2Q_6$, where each Q is independently selected from a group consisting of methyl and chlorine and the disilane contains two to four methyl substituents per molecule; 15 to 25 weight percent silmethylenes described by formula $Q_3SiCH_2SiQ_3$, where Q is as previously described and the silmethylene contains two to four methyl substituents per molecule; silalkylenes described by formula $Q_3Si(SQ_2)_a(CH_2)_b(SiO_2)_cSiQ_3$, where Q is as previously described, the silalkylene contains two to four methyl substituents per molecule, a=0 to 4, b=1 to 3, c=0 to 4, and a+c≧1; 5 to 15 weight percent of other high-boiling silicon-containing compounds; catalysts carry over from the direct process such as copper and compounds of copper; particulate containing silicon; and low levels of metals such as aluminum, calcium, iron, and compounds thereof. For example, a typically weight percent composition of a high-boiling fraction resulting from the reaction of methyl chloride with silicon metalloid is 4 wt % $Me_2ClSiSiClMe_2$, 31 wt % $Me_2ClSiSiMeCl_2$, 46 wt % $MeCl_2SiSiMeCl_2$, 1 wt % $Me_2ClSiCH_2SiClMe_2$, 3 wt % $Me_2ClSiCH_2SiCl_2Me$, 7 wt % $MeCl_2SiCH_2SiCl_2Me$, and 9 wt % other.

In the mixture of the present process, weight percent of low-boiling fraction to the high-boiling fraction is not critical. Generally, a mixture where the low-boiling fraction is about 0.1 to 95 weight percent of the mixture is considered useful. Preferred is where the low-boiling fraction is about 30 to 50 weight percent of the mixture.

The mixture is contacted with hydrogen gas at a pressure of about 345 kPa to 68,900 kpa. Preferred is a hydrogen gas pressure of about 2,000 kPa to 10,000 kPa. More preferred is a hydrogen gas pressure of about 4,000 kPa to 7,500 kPa.

The catalyst useful in the present process are those catalyst effective in promoting conversion of the polymeric silicon containing compounds to monosilanes. Generally, Lewis Acids or equivalents may be used as a catalyst. Examples of catalyst effective in promoting conversion of the polymeric silicon containing compounds to monosilanes include aluminum trichloride, iron trichloride, antimony pentachloride, zirconium tetrachloride, potassium aluminum tetrachloride, quaternary phosphonium halides, quaternary ammonium halides, ammonium halides, cuprous chloride, boric acid, and boron halides. The catalyst can be heterogeneous catalysts, for example, alumina, aluminosilicates, zeolites silica and activated carbon. A preferred catalyst is aluminum trichloride.

The amount of catalyst useful in the present process is any amount effective in promoting conversion of the polymeric silicon containing compounds to monosilanes. Preferably, the catalyst concentration is within a range of about 0.05 to 15 weight percent of the high-boiling fraction comprising the polymeric silicon containing compounds. Most preferable, the catalyst concentration is within a range of about 0.5 to 5 weight percent of the high-boiling fraction comprising the polymeric silicon containing compounds.

The catalyst may be added to the mixture as a separate component or preferably may be present from conducting the direct process. When the catalyst is present in the mixture from the direct process, additional catalyst may be added to the mixture if required to promote conversion of the polymeric silicon containing compounds to monosilanes. Preferably, the additional catalyst added to the mixture is the same as the catalyst present from the direct process. However it is within the scope of the present invention to add a different catalyst to the mixture than the catalyst present from the direct process.

When the catalyst is aluminum trichloride the concentration is within a range of about 0.05 to 15 weight percent of the high-boiling fraction comprising the polymeric silicon containing compounds. Most preferable, the aluminum trichloride concentration is within a range of about 0.5 to 5 weight percent of the high-boiling fraction comprising the polymeric silicon containing compounds.

The aluminum trichloride may be added to the process as the compound or may be formed in situ by the addition of materials that form aluminum trichloride. All or a portion of the catalytic amount of aluminum trichloride may be formed in situ during conduct of the direct process and distillation to form the high-boiling fraction. The source of the aluminum and chlorine necessary to form the aluminum trichloride can be the raw materials used in the direct process, particularly the silicon metalloid and methyl chloride feed. The aluminum trichloride catalyst amount can be a combination of added aluminum trichloride and in situ formed aluminum trichloride remaining in the mixture as isolated from the direct process.

The present process can be conducted at a temperature within a range of about 150° C. to 500° C. Preferred is a temperature within a range of about 275° C. to 425° C. Most preferred is a temperature within a range of about 300° C. to 350° C.

Monosilanes described by formula $$Me_aH_bSiCl_{4-a-b},$$

are recovered from the present process; where Me is methyl, a=0–4, b=0–3, and a+b=0–4. Preferred monosilanes are selected from a group consisting of dimethyldichlorosilane and methyldichlorosilane. The monosilanes can be separated by standard methods for separating liquid mixtures, for example, distillation.

The following examples are provided to illustrate the present invention. These examples are not intended to limit the claims herein.

EXAMPLE 1

The ability to convert a high-boiling fraction with in situ formed aluminum trichloride as catalyst was evaluated in a stirred-tank batch reactor. The reactor was a 600 ml, pneumatically stirred, Parr Bomb reactor. A mixture comprising about 37 gram of low-boiling distillation fraction (LBF) and 56.5 gram of a high-boiling distillation fraction (HBF) from the direct process for the preparation of methylchlorosilanes by the reaction of methyl chloride with silicon metalloid was added to the reactor. The aluminum trichloride present in the mixture was in situ formed during preparation and isolation of monosilanes. Hydrogen gas at 2758 kPa was added to the reactor while stirring and the reactor was heated to about 340° C. for about 1.5 hours. A sample from the reactor was analyzed by gas chromatography (GC) using a thermal conductivity detector (TCD). The LBF components, HBF components, initial component weight percent and analysis results indicated by the final component weight percent are reported in Table 1.

TABLE 1

Mixture Composition

| Components | Initial Component Weight % | Final Component Weight % |
|---|---|---|
| LBF | | |
| MeCl | 1.48 | 0.05 |
| MeH$_2$SiCl | 0.35 | 3.88 |
| Me$_4$Si | 7.05 | 1.21 |
| HSiCl$_3$ | 5.16 | 1.03 |
| Me$_2$HSiCl | 16.33 | 4.97 |
| MeHSiCl$_2$ | 0.15 | 17.32 |
| Me$_3$SiCl | 0 | 4.42 |
| MeSiCl$_3$ | 0 | 6.73 |
| Me$_2$SiCl$_2$ | 5 | 24.63 |
| HBF | | |
| Me$_2$ClSiSiClMe$_2$ | 3.39 | 0.17 |
| Me$_2$ClSiSiMeCl$_2$ | 16.84 | 0 |
| MeCl$_2$SiSiMeCl$_2$ | 21.73 | 0 |
| Me$_2$ClSiCH$_2$SiClMe$_2$ | 0 | 0.17 |
| Me$_2$ClSiCH$_2$SiCl$_2$Me | 5 | 1.25 |
| MeCl$_2$SiCH$_2$SiCl$_2$Me | 0 | 1.73 |

EXAMPLE 2

The ability to convert a high-boiling fraction with in situ formed aluminum trichloride as catalyst was evaluated in a stirred-tank batch reactor. The reactor was a 600 ml, pneumatically stirred, Parr Bomb reactor. A mixture comprising about 40.6 gram of low-boiling distillation fraction (LBF) and 47.4 gram of a high-boiling distillation fraction (HBF) from the direct process for the preparation of methylchlorosilanes by the reaction of methyl chloride with silicon metalloid was added to the reactor. The aluminum trichloride present in the mixture was in situ formed during preparation and isolation of monosilanes. Hydrogen gas at 2758 kPa was added to the reactor while stirring and the reactor was heated to about 340° C. for about 1.5 hours. A sample from the reactor was analyzed by gas chromatography (GC) using a thermal conductivity detector (TCD). The LBF components, HBF components, initial component weight percent and analysis results indicated by the final component weight percent are reported in Table 2.

TABLE 2

Mixture Composition

| Components | Initial Component Weight % | Final Component Weight % |
|---|---|---|
| LBF | | |
| MeCl | 2.12 | 0.05 |
| MeH$_2$SiCl | 0.54 | 4.91 |
| Me$_4$Si | 9.94 | 0.09 |
| HSiCl$_3$ | 7.04 | 0.97 |
| Me$_2$HSiCl | 22.53 | 7.02 |
| MeHSiCl$_2$ | 0.21 | 20.55 |
| Me$_3$SiCl | 0 | 3.63 |
| MeSiCl$_3$ | 0 | 7.70 |
| Me$_2$SiCl$_2$ | 0 | 31.50 |
| HBF | | |
| Me$_2$ClSiSiClMe$_2$ | 1.61 | 0.10 |
| Me$_2$ClSiSiMeCl$_2$ | 13.77 | 0.02 |
| MeCl$_2$SiSiMeCl$_2$ | 20.47 | 0 |
| Me$_2$ClSiCH$_2$SiClMe$_2$ | 0.31 | 0.14 |
| Me$_2$ClSiCH$_2$SiCl$_2$Me | 1.55 | 1.22 |
| MeCl$_2$SiCH$_2$SiCl$_2$Me | 3.29 | 1.70 |

We claim:

1. A process for converting a high-boiling fraction resulting from the reaction of methyl chloride with silicon metalloid to monosilanes, the process comprising:

(A) forming a mixture comprising a low-boiling fraction comprising monosilanes having a boiling point below about 45° C. resulting from the reaction of methyl chloride with silicon metalloid and a high-boiling fraction comprising polymeric silicon containing compounds having a boiling point above about 80° C. resulting from the reaction of methyl chloride with silicon metalloid; and (B) contacting the mixture with hydrogen gas at a pressure of about 345 kPa to 68,900 kPa in the presence of a catalyst effective in promoting conversion of the polymeric silicon containing compounds to monosilanes at a temperature within a range of about 150° C. to 500° C.

2. A process according to claim 1 further comprising (C) recovering monosilanes of formula $$Me_aH_bSiCl_{4-a-b},$$

where Me is methyl, a=0–4, b=0–3, and a+b=0–4.

3. A process according to claim 2, where the monosilane is selected from a group consisting of dimethyldichlorosilane and methyldichlorosilane.

4. A process according to claim 1, where the high-boiling fraction is a distillation fraction resulting from the distillation of the reaction product of methyl chloride with silicon metalloid.

5. A process according to claim 1, where the low-boiling fraction is a distillation fraction resulting from the distillation of the reaction product of methyl chloride with silicon metalloid.

6. A process according to claim 1, where the low-boiling fraction is about 0.1 to 95 weight percent of the mixture comprising the low-boiling fraction and high-boiling fraction.

7. A process according to claim 1, where the low-boiling fraction is about 30 to 50 weight percent of the mixture comprising the low-boiling fraction and high-boiling fraction.

8. A process according to claim 1, where the hydrogen gas pressure is within a range of about 2000 kPa to 10,000 kPa.

9. A process according to claim 1, where the hydrogen gas pressure is within a range of about 4,000 kPa to 7,500 kPa.

10. A process according to claim 1, where the catalyst is aluminum trichloride.

11. A process according to claim 10, where the aluminum trichloride concentration is within a range of about 0.01 to 15 weight percent of the high-boiling fraction.

12. A process according to claim 10, where aluminum trichloride concentration is within a range of about 0.5 to 5 weight percent of the high-boiling fraction.

13. A process according to claim 10, where at least a portion of the aluminum trichloride is formed in situ during formation of the high-boiling fraction.

14. A process according to claim 10, where at least a portion of the aluminum trichloride is formed in situ during formation of the low-boiling fraction.

15. A process according to claim 1, where the temperature is within a range of about 275° C. to 425° C.

16. A process according to claim 1, where the temperature is within a range of about 300° C. to 350° C.

17. A process according to claim 1, where the catalyst is different from the in situ formed catalyst during conduct of the direct process.

18. A process for converting a high-boiling fraction resulting from the reaction of an methyl chloride with silicon metalloid to monosilanes, the process comprising:

(A) forming a mixture comprising a low-boiling fraction comprising monosilanes having a boiling point below about 45° C. resulting from the reaction of methyl chloride with silicon metalloid and a high-boiling fraction comprising polymeric silicon containing compounds having a boiling point above about 80° C. resulting from the reaction of methyl chloride with silicon metalloid; and (B) contacting the mixture with hydrogen gas at a pressure of about 345 kPa to 68,900 kPa in the presence of aluminum trichloride to promote conversion of the polymeric silicon containing compounds to monosilanes at a temperature within a range of about 150° C. to 500° C.

19. A process according to claim 18, where the aluminum trichloride concentration is within a range of about 0.01 to 15 weight percent of the high-boiling fraction.

* * * * *